(12) United States Patent
Oniduka et al.

(10) Patent No.: US 11,876,431 B2
(45) Date of Patent: Jan. 16, 2024

(54) MAGNETIC BEARING, DRIVE DEVICE EQUIPPED WITH THE SAME, AND PUMP

(71) Applicant: IWAKI CO., LTD., Tokyo (JP)

(72) Inventors: Toshiki Oniduka, Iruma-gun (JP); Shinichirou Koreeda, Iruma-gun (JP); Toshiaki Kamei, Sayama (JP); Takuya Seki, Sayama (JP)

(73) Assignee: IWAKI CO., LTD., Tokyo (JP)

( * ) Notice: Subject to any disclaimer, the term of this patent is extended or adjusted under 35 U.S.C. 154(b) by 136 days.

(21) Appl. No.: 17/438,083

(22) PCT Filed: Jan. 10, 2020

(86) PCT No.: PCT/JP2020/000656
§ 371 (c)(1),
(2) Date: Sep. 10, 2021

(87) PCT Pub. No.: WO2020/183884
PCT Pub. Date: Sep. 17, 2020

(65) Prior Publication Data
US 2022/0247266 A1 Aug. 4, 2022

(30) Foreign Application Priority Data

Mar. 14, 2019 (JP) ................................ 2019-046982
Aug. 22, 2019 (JP) ................................ 2019-151775

(51) Int. Cl.
*H02K 7/09* (2006.01)
*A61M 60/822* (2021.01)
(Continued)

(52) U.S. Cl.
CPC ............ *H02K 7/09* (2013.01); *A61M 60/196* (2021.01); *A61M 60/216* (2021.01);
(Continued)

(58) Field of Classification Search
CPC ........ H02K 7/09; H02K 7/14; F16C 32/0465; F16C 32/0468; F16C 32/0493
See application file for complete search history.

(56) References Cited

U.S. PATENT DOCUMENTS 6,268,674 B1 * 7/2001 Takahashi ........... F16C 32/0468
310/90.5

FOREIGN PATENT DOCUMENTS

JP         S59-43220 A      3/1984
JP         S5943220 A  *   3/1984 .......... F16C 32/0465
(Continued)

OTHER PUBLICATIONS

JP-4557245-B2_translate (Year: 2010).*
(Continued)

*Primary Examiner* — Tulsidas C Patel
*Assistant Examiner* — Mohammed Ahmed Qureshi
(74) *Attorney, Agent, or Firm* — Oliff PLC (57) ABSTRACT

A magnetic bearing contactlessly supporting a rotor by magnetic force includes: a bearing rotor member made of a magnetic material; and a bearing stator member arranged around bearing rotor member. The bearing stator member includes a core made of a magnetic material and a coil wound around the core. A longitudinal cross-sectional shape of the core has a first part extending in a first direction orthogonal to a direction opposed to the bearing rotor member and wound around with the coil, a pair of second parts extending from both end portions in the first direction of first part to the bearing rotor member side and subsequently extending in a direction approaching each other in the first direction, and a pair of third parts extending from respective distal end portions of the pair of second parts toward the bearing rotor member side. The bearing rotor member also includes a permanent magnet.

11 Claims, 9 Drawing Sheets

(51) Int. Cl.
  *F16C 32/04* (2006.01)
  *H02K 7/14* (2006.01)
  *A61M 60/422* (2021.01)
  *A61M 60/216* (2021.01)
  *A61M 60/196* (2021.01)

(52) U.S. Cl.
  CPC ........ *A61M 60/422* (2021.01); *A61M 60/822* (2021.01); *F16C 32/0465* (2013.01); *H02K 7/14* (2013.01); *F16C 32/0468* (2013.01); *F16C 32/0493* (2013.01)

(56) References Cited

FOREIGN PATENT DOCUMENTS

| | | |
|---|---|---|
| JP | S60-73929 U | 5/1985 |
| JP | H11-325073 A | 11/1999 |
| JP | 2005-121157 A | 5/2005 |
| JP | 4557245 B2 * | 10/2010 .......... F16C 32/0465 |

OTHER PUBLICATIONS

JP-S5943220-A_translate (Year: 1984).*
Mar. 10, 2020 Written Opinion issued in International Patent Application No. PCT/JP2020/000656.
Mar. 10, 2020 International Search Report issued in International Patent Application No. PCT/JP2020/000656.

* cited by examiner

A-A' cross section

B-B' cross section

C-C′ cross section

MAGNETIC BEARING, DRIVE DEVICE EQUIPPED WITH THE SAME, AND PUMP

TECHNICAL FIELD

The present invention relates to a magnetic bearing, a drive device equipped with the same, and a pump.

BACKGROUND ART

Figure 20:
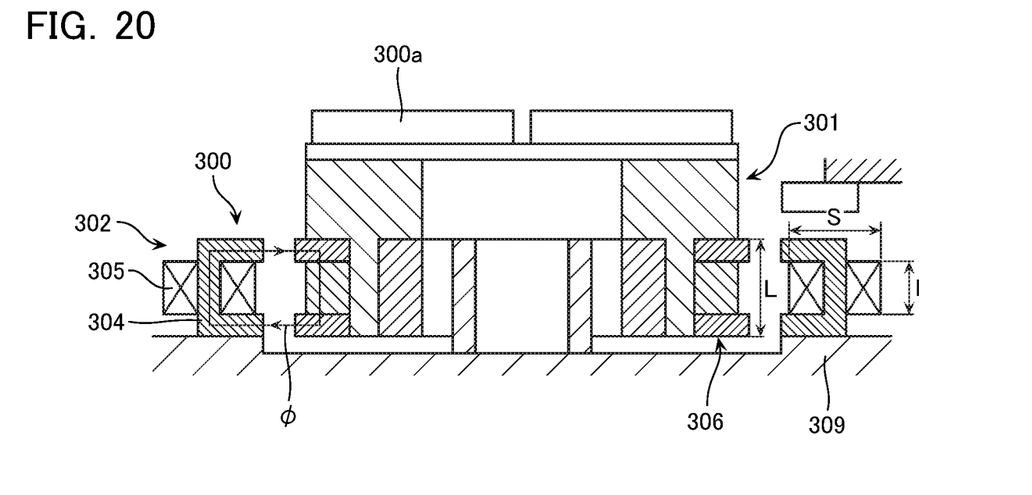
FIG. 20 is a longitudinal cross-sectional view schematically illustrating an overall configuration of a conventional magnetic bearing.

A magnetic bearing that supports a load and the like of an impeller of a pump device contactlessly by magnetic force is known (see, for example, Patent Literature 1). As illustrated in FIG. 20, such a magnetic bearing 300 is constituted of, for example, a bearing rotor member 306 disposed in a rotor 301 including an impeller 300a and a bearing stator member 302 secured to a housing 309.

PRIOR ART LITERATURE

Patent Literature

Patent Literature 1: Japanese Unexamined Patent Application Publication No. 2005-121157

SUMMARY OF INVENTION

Problem to be Solved by Invention

In this type of magnetic bearing 300, a restoring force to a specified position with respect to the rotor 301 works by a magnetic flux φ passing through a magnetic circuit formed by a U-shaped core 304 constituting the bearing stator member 302 and the bearing rotor member 306. It is known that this restoring force is greater, for example, when a length of the core 304 of the bearing stator member 302 and a thickness L in a thrust direction of the bearing rotor member 306 are approximately equal and as thin as possible.

On the other hand, the magnetic flux φ is controlled by a coil 305 of the bearing stator member 302. In order to improve responsiveness, it is preferred to decrease an inductance of the coil 305 as much as possible. The inductance of a coil is proportional to a cross-sectional area S of the coil and inversely proportional to a coil length l. In view of this, in order to improve the responsiveness of the coil 305, it is necessary to wind the coil 305 around the core 304 so as to decrease the cross-sectional area S of the coil 305 and lengthen the length l of the coil 305.

However, when the coil length l lengthens, the thickness L in the thrust direction of the bearing rotor member 306 of the rotor 301 also increases. Therefore, the restoring force of the rotor 301 decreases. In particular, a restoring torque decreases when the rotor 301 inclines, while a dimension (size) in thrust direction of the magnetic bearing 300 increases.

The present invention has been made in consideration of the above situation, and an object of the present invention is to provide a magnetic bearing, a drive device equipped with the magnetic bearing, and a pump which can improve responsiveness while strengthening a restoring force of a rotor.

Solution to Problem

A magnetic bearing according to the present invention contactlessly supports a rotor by magnetic force. The magnetic bearing includes a bearing rotor member made of a magnetic material disposed in the rotor and a bearing stator member arranged around the bearing rotor member. The bearing stator member includes a core made of a magnetic material and a coil wound around the core. A longitudinal cross-sectional shape of the core has a first part extending in a first direction orthogonal to a direction opposed to the bearing rotor member and wound around with the coil, a pair of second parts extending from both end portions in the first direction of the first part to the bearing rotor member side and subsequently extending in a direction approaching each other in the first direction, and a pair of third parts extending from respective distal end portions of the pair of second parts toward the bearing rotor member side. The bearing rotor member includes a permanent magnet supplying a bias magnetic flux to a magnetic circuit formed by the bearing rotor member and the core.

In one embodiment of the invention, a length in the first direction of the coil is greater than a distance between opposed surfaces in the first direction of the pair of third parts.

In another embodiment of the invention, a distance between surfaces on opposite sides of the opposed surfaces in the first direction of the pair of third parts is smaller than a length in the first direction of the first part.

In yet another embodiment of the invention, the distance between surfaces on opposite sides of the opposed surfaces in the first direction of the pair of third parts is approximately equal to a length in the first direction of the bearing rotor member opposed to the third parts. In yet another embodiment of the invention, the bearing rotor member includes: the permanent magnet in a circular shape and a pair of circular yokes arranged so as to sandwich the permanent magnet in the first direction. A longitudinal cross-sectional shape of the pair of yokes has a pair of fourth parts covering both end surfaces in the first direction of the permanent magnet and extending to an opposite side of the bearing stator member and a pair of fifth parts extending from end portions of the pair of fourth parts on an opposite side of the bearing stator member in a direction approaching each other in the first direction. A first gap is formed between the fifth parts and the permanent magnet, and a second gap is provided between respective distal end portions of the pair of fifth parts opposed to each other.

In yet another embodiment of the invention, a plurality of the bearing stator members are arranged on an outside in a radial direction of the bearing rotor member and are each opposed to the bearing rotor member in the radial direction.

In yet another embodiment of the invention, a plurality of the bearing stator members are arranged on at least one side in an axial direction of the bearing rotor member and are each opposed to the bearing rotor member in the axial direction.

A drive device according to the present invention includes a rotor, a magnetic bearing supporting the rotor by magnetic force, and a drive mechanism rotatably driving the rotor. The magnetic bearing includes a bearing rotor member made of a magnetic material disposed in the rotor and a bearing stator member arranged around the bearing rotor member. The bearing stator member includes a core made of a magnetic material and a coil wound around the core. A longitudinal cross-sectional shape of the core has a first part extending in a first direction orthogonal to a direction opposed to the bearing rotor member and wound around with the coil, a pair of second parts extending from both end portions in the first direction of the first part to the bearing rotor member side and subsequently extending in a direction approaching each other in the first direction, and a pair of third parts extending from respective distal end portions of the pair of second parts toward the bearing rotor member side. The bearing rotor member includes a permanent magnet supplying a bias magnetic flux to a magnetic circuit formed by the bearing rotor member and the core.

In one embodiment of the invention, the bearing rotor member includes the permanent magnet in a circular shape, and a pair of circular yokes arranged so as to sandwich the permanent magnet in the first direction. A longitudinal cross-sectional shape of the pair of yokes has a pair of fourth parts covering both end surfaces in the first direction of the permanent magnet and extending to an opposite side of the bearing stator member, and a pair of fifth parts extending from end portions of the pair of fourth parts on an opposite side of the bearing stator member in a direction approaching each other in the first direction. A first gap is formed between the fifth parts and the permanent magnet, and a second gap is provided between respective distal end portions of the pair of fifth parts opposed to each other.

In another embodiment of the invention, the drive mechanism includes a driven member arranged on an inside in a radial direction of the bearing rotor member in the rotor, and a drive unit arranged on an inside of the driven member and magnetically coupled with the driven member to drive the rotor.

A pump according to the present invention includes a rotor, a magnetic bearing supporting the rotor by magnetic force, a drive mechanism rotatably driving the rotor, and a pump mechanism that includes an impeller attached to the rotor. The magnetic bearing includes a bearing rotor member made of a magnetic material disposed in the rotor and a bearing stator member arranged around the bearing rotor member. The bearing stator member includes a core made of a magnetic material and a coil wound around the core. A longitudinal cross-sectional shape of the core has a first part extending in a first direction orthogonal to a direction opposed to the bearing rotor member and wound around with the coil, a pair of second parts extending from both end portions in the first direction of the first part to the bearing rotor member side and subsequently extending in a direction approaching each other in the first direction, and a pair of third parts extending from respective distal end portions of the pair of second parts toward the bearing rotor member side. The bearing rotor member includes a permanent magnet supplying a bias magnetic flux to a magnetic circuit formed by the bearing rotor member and the core. In one embodiment of the invention, the bearing rotor member includes the permanent magnet in a circular shape, and a pair of circular yokes arranged so as to sandwich the permanent magnet in the first direction. A longitudinal cross-sectional shape of the pair of yokes has a pair of fourth parts covering both end surfaces in the first direction of the permanent magnet and extending to an opposite side of the bearing stator member; and a pair of fifth parts extending from end portions of the pair of fourth parts on an opposite side of the bearing stator member in a direction approaching each other in the first direction. A first gap is formed between the fifth parts and the permanent magnet, and a second gap is provided between respective distal end portions of the pair of fifth parts opposed to each other.

Effect of Invention

The present invention can improve responsiveness while strengthening a restoring force of a rotor.

MODES FOR CARRYING OUT THE INVENTION

The following describes in detail a magnetic bearing, a drive device equipped with the magnetic bearing, and a pump according to the embodiments of the present invention by referring to the accompanying drawings. However, the following embodiments do not limit the invention according to each claim, and all combinations of features described in the embodiments are not necessarily essential to the solution of the invention. Further, in the following embodiments, components that are same or correspond to each other will be denoted by the same reference numerals, and an overlapped description thereof will be omitted. Further, in the embodiments, the scale and dimensions of each component may be exaggerated, or some components may be omitted.

First Embodiment

[Configuration of Magnetic Bearing, Drive Device, and Pump]

Figure 1:
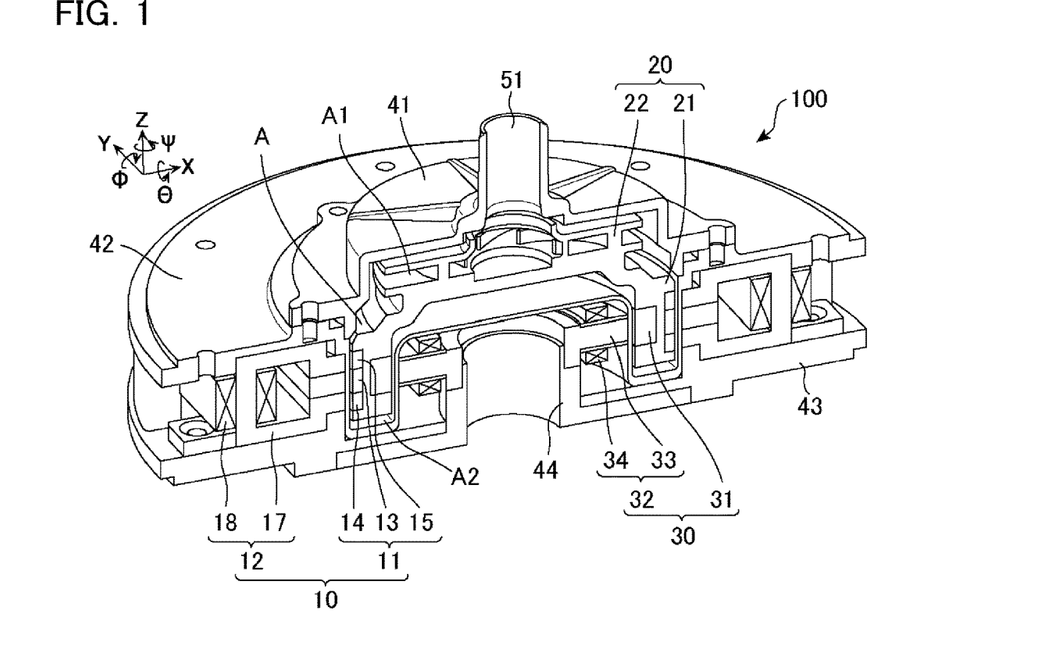
FIG. 1 is a cutout perspective view schematically illustrating an overall configuration of a pump to which a magnetic bearing and a drive device equipped with the magnetic bearing according to a first embodiment of the present invention are applied.
Figure 2:
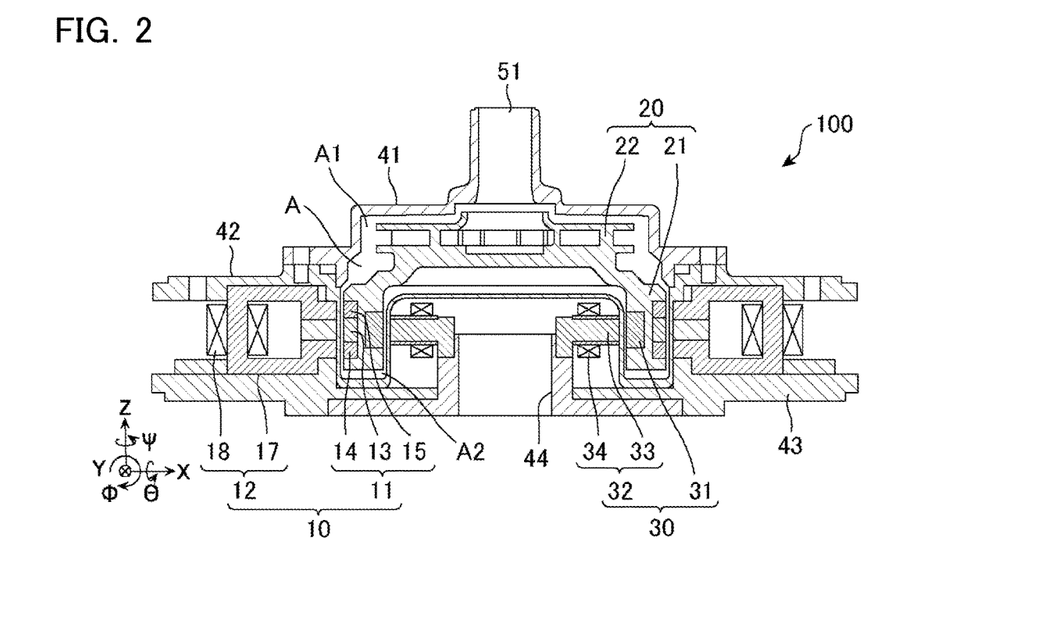
FIG. 2 is a longitudinal cross-sectional view schematically illustrating the pump.
Figure 3:
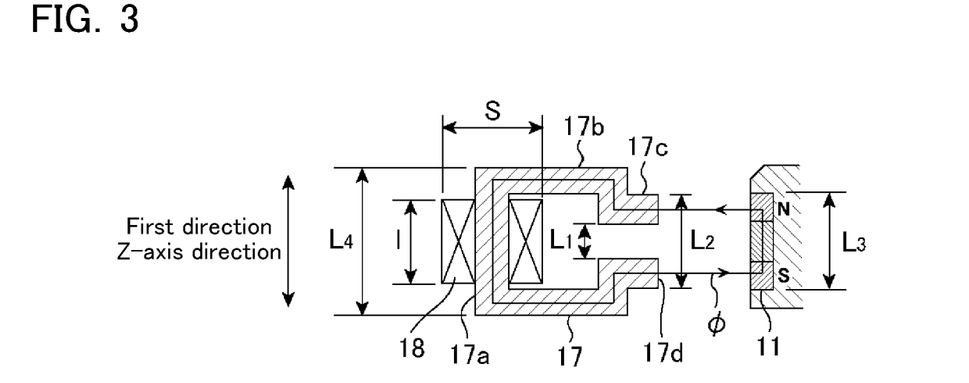
FIG. 3 is an enlarged longitudinal cross-sectional view schematically illustrating the magnetic bearing.

FIG. 1 is a partially cutout perspective view schematically illustrating an overall configuration of a pump 100 to which a magnetic bearing 10 and a drive device 90 equipped with the magnetic bearing 10 according to a first embodiment are applied. FIG. 2 is a longitudinal cross-sectional view schematically illustrating the pump 100, FIG. 3 is an enlarged longitudinal cross-sectional view schematically illustrating the magnetic bearing 10, and FIG. 4 is a top view schematically illustrating an overall configuration of the drive device 90.

Figure 4:
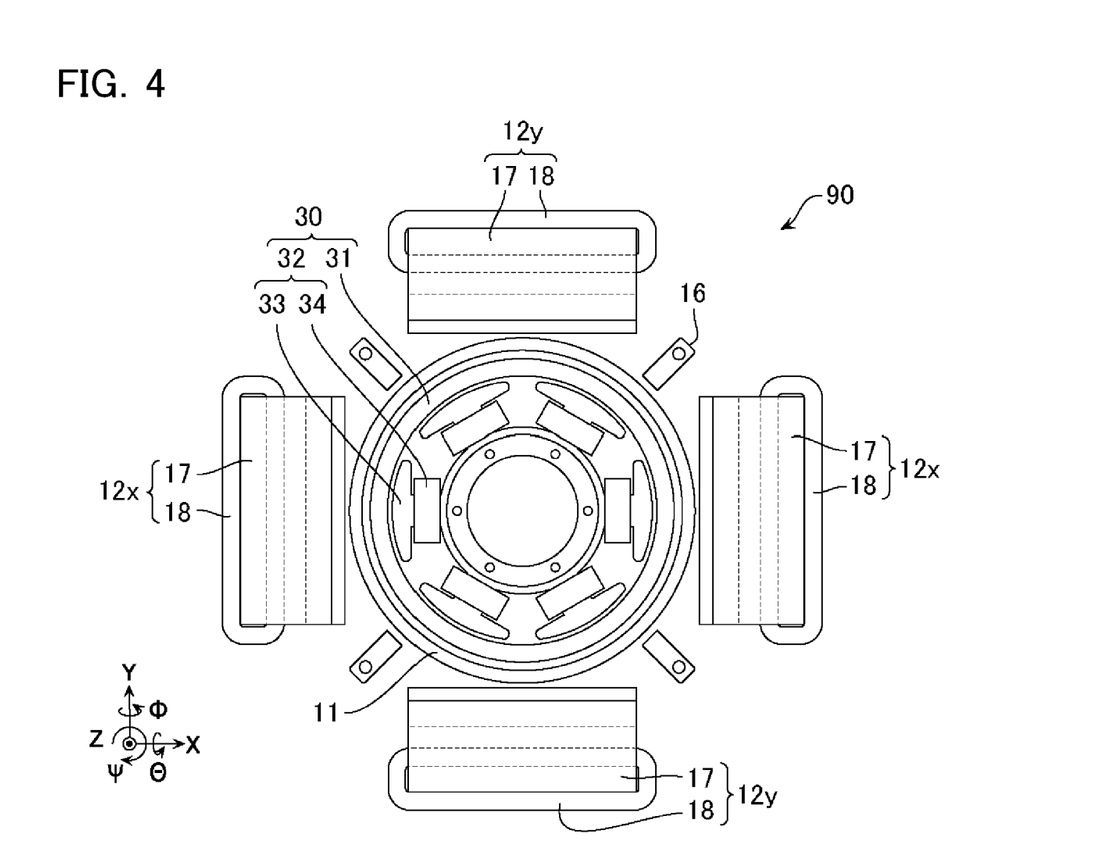
FIG. 4 is a top view schematically illustrating an overall configuration of the drive device.

As illustrated in FIG. 1 to FIG. 4, the pump 100 according to the first embodiment is used for, for example, a pump for an artificial heart and the like, and includes a rotor 20, the magnetic bearing 10 that contactlessly supports the rotor 20 by magnetic force, and a drive mechanism 30 that rotatably drives the rotor 20. Although this example illustrates the pump 100, the rotor 20, the magnetic bearing 10, and the drive mechanism 30 can be regarded as the drive device (actuator) 90, as illustrated in FIG. 4, if only a function of them that rotatably drives the rotor 20 is focused.

Note that, in the following description, a rotation axis direction of the rotor 20 is referred to as a Z direction (also referred to as a thrust direction), a radial direction of the rotor 20 is referred to as an X direction and a Y direction (also referred to as a radial direction), and a rotation direction around the Z-axis (rotation axis), a rotation direction around the X-axis, and a rotation direction around the Y-axis are referred to as a Ψ direction, a Θ direction, and a Φ direction, respectively. Further, the X-axis, the Y-axis and the Z-axis are assumed to be mutually orthogonal.

The rotor 20 is formed of a non-magnetic body, such as resin, as a whole, and is made by integrally forming an annular bearing/drive unit 21 disposed at one end of the Z-axis direction and an impeller 22 disposed at the other end. The rotor 20 is housed in a sealed space A formed by a front casing 41 and a rear casing 42. The sealed space A contains a pump chamber A1 that houses the impeller 22 and an annular space A2 that houses the bearing/drive unit 21. The impeller 22 constitutes a pump mechanism together with the pump chamber A1. The front casing 41 has a suction port 51 that is communicated with the pump chamber A1 disposed in a center portion of a front face, and the front casing 41 has a discharge port (not illustrated) that is communicated with the pump chamber A1 disposed on a side surface.

The magnetic bearing 10 has a bearing rotor member 11 made of an annular magnetic material and a bearing stator member 12. The bearing rotor member 11 is mounted on an outer peripheral side of the bearing/drive unit 21 of the rotor 20. The bearing stator member 12 is arranged on an outside in the radial direction of the bearing rotor member 11 at a predetermined interval from the bearing rotor member 11. The bearing stator member 12 is mounted between an annular yoke base 43 and an outer peripheral portion of the rear casing 42.

The drive mechanism 30 has a driven magnet 31 as an annular driven member and a motor stator 32 as a drive unit. The driven magnet 31 is mounted on an inner peripheral side of the bearing/drive unit 21 of the rotor 20. The motor stator 32 is arranged on an inside in the radial direction of the driven magnet 31 at a predetermined interval from the driven magnet 31. In this example, the driven magnet 31 is configured as, for example, a neodymium magnet magnetized in four poles in the radial direction, and the motor stator 32 is configured as a stator of a three-phase brushless motor that has a motor stator core 33 that is a magnetic body having 6 salient poles and a motor coil 34 wound around each salient pole of the motor stator core 33. The motor stator 32 is mounted between a housing 44 secured to an inside of the yoke base 43 and a center portion of the rear casing 42.

Next, the details of the magnetic bearing 10 will be described.

The bearing rotor member 11 of the magnetic bearing 10 has a permanent magnet 13 made of a neodymium magnet formed in, for example, a circular shape, and circular yokes 14 and 15 made of electromagnetic soft iron that are concentric with the permanent magnet 13 and arranged so as to sandwich the permanent magnet 13 in the thrust direction (Z-axis direction). The permanent magnet 13 is magnetized such that, for example, an N-pole and an S-pole are opposed in the thrust direction and have the same polarity over a whole circumference in a circumferential direction.

On the other hand, in this embodiment, the bearing stator member 12 of the magnetic bearing 10 is arranged at 4 portions in the circumferential direction of the bearing rotor member 11 at intervals of an angle of 90° as illustrated in FIG. 4. Among them, a pair of bearing stator members 12x opposed in the X-axis direction control a position in the X-axis direction and an angle in the Φ direction of the rotor 20, and a pair of bearing stator members 12y opposed in the Y-axis direction control a position in the Y-axis direction and an angle in the Θ direction of the rotor 20. Further, the bearing stator members 12x and 12y control a height in the Z-axis direction. Note that on the yoke base 43, a plurality of displacement sensors 16 (4 in here) that detect displacements in the radial direction, the thrust direction, and each rotation direction of the bearing rotor member 11 are arranged so as to each intersect the X direction and the Y direction at an angle of 45°. Although examples of the displacement sensor 16 include an eddy current type sensor, the displacement sensor 16 is not limited to this and various kinds of sensors can be employed.

The bearing stator member 12 has a core 17 made of a magnetic material, such as a stacked electromagnetic steel plate, and a coil 18 wound around the core 17. The core 17 has a longitudinal cross-sectional shape that is approximately C-shaped with the bearing rotor member 11 side as an open end. More specifically, as illustrated in FIG. 3, the longitudinal cross-sectional shape of the core 17 includes a first part 17a, a pair of second parts 17b, and a pair of third parts 17c. The first part 17a extends in a first direction (Z-axis direction in this example) orthogonal to a direction opposed to the bearing rotor member 11 and is wound around with the coil 18. The pair of second parts 17b extend from both end portions in the Z-axis direction of the first part 17a to the bearing rotor member 11 side, and subsequently extend in a direction approaching each other in the Z-axis direction. The pair of third parts 17c extend from respective distal end portions of the pair of second parts 17b toward the bearing rotor member 11 side. In other words, in the longitudinal cross-sectional shape, the core 17 has a pair of key-shaped parts at a C-shaped open end part (see FIG. 20) that should originally extend from both ends in the Z-axis direction of the first part 17a wound around with the coil 18 toward the bearing rotor member 11 and has a shape in which the open ends are approached each other.

With such a shape, a length l in the Z-axis direction of the coil 18 can be made greater than a distance L1 between opposed surfaces in the Z-axis direction of the pair of third parts 17c on the open end side of the core 17. Further, a width on the open end side of the core 17, that is, a distance L2 between surfaces on opposite sides of the opposed surfaces in the Z-axis direction of the pair of third parts 17c is smaller than a length L4 in the original Z-axis direction of the core 17 and approximately equal to a length L3 in the Z-axis direction of the bearing rotor member 11.

[Operation of Magnetic Bearing, Drive Device, and Pump]

Next, an operation of the pump 100 configured as described above to which the magnetic bearing 10 and the drive device 90 equipped with the magnetic bearing 10 are applied will be described.

The bearing rotor member 11 and the core 17 of the bearing stator member 12 constituting the magnetic bearing 10 are made of a magnetic material and form a magnetic circuit. The permanent magnet 13 of the bearing rotor member 11 supplies a bias magnetic flux to this magnetic circuit. A control circuit (not illustrated) controls a current flowing through the coil 18 so as to correct the displacements in the XYZ-axes directions of the rotor 20 and an inclination in the Φ and Θ directions that are detected by the displacement sensors 16 to adjust a control magnetic flux generated by the coil 18. This allows the rotor 20 to maintain a predetermined position and a predetermined posture by the magnetic bearing 10 and to be supported in a non-contact state.

When the motor coil 34 of the motor stator 32 is supplied with three-phase AC power in this state, the three-phase brushless motor operates and the rotor 20 rotates. When the rotor 20 rotates, the impeller 22 also rotates. Accordingly, a transfer fluid is introduced into the pump chamber A1 through the suction port 51, and the transfer fluid is discharged through the discharge port.

Effects of Embodiment

Here, as described above, a restoring force of the position and inclination by the magnetic bearing 10 of the rotor 20 increases when the length L2 in the Z-axis direction of the open end (third parts 17c) of the bearing stator member 12 is approximately equal to the length L3 in the Z-axis direction of the bearing rotor member 11, and the length L3 in the Z-axis direction of the bearing rotor member 11 is short as well. In this respect, with the magnetic bearing 10 according to the embodiment, since the length L2 in the Z-axis direction of the parts of the open end (third parts 17c) opposed to the bearing rotor member 11 can be made shorter compared with a conventional C-shaped core 304 illustrated in FIG. 20, the length L3 in the Z-axis direction of the bearing rotor member 11 can be made shorter than the conventional length while the number of turns N of the coil 18 is maintained. This can ensure the sufficient restoring force. Note that, in order to maximize an attraction force of the permanent magnet 13, it is preferred that the distance L1 between the third parts 17c of the core 17 and a height in the Z-axis direction of the permanent magnet 13 is approximately equal and besides a width in the Z-axis direction of each of the third parts 17c (salient pole) of the core 17 is approximately equal to a thickness in the Z-axis direction of the yokes 14 and 15.

Further, as described above, in order to improve responsiveness of the magnetic bearing 10, it is necessary to decrease an inductance of the coil 18 as much as possible. In this respect, with the magnetic bearing 10 according to the embodiment, since the length L4 of the first part 17a around which the coil 18 of the core 17 is wound can be sufficiently ensured, the length l in the Z-axis direction of the coil 18 can be made longer and a cross-sectional area S of the coil 18 can be made smaller. This can reduce the inductance of the coil 18 to improve the responsiveness.

Note that, although an outer peripheral surface of the bearing rotor member 11 is configured as a curved surface as illustrated in FIG. 4, magnetic pole surfaces 17d of the core 17 are formed as a planar surface. Specifically, the magnetic pole surfaces 17d are formed on the same planar surface extending in the X-axis direction or the Y-axis direction and the Z-axis direction.

Generally, when the magnetic pole surfaces 17d of the core 17 are configured as curved surfaces along the outer peripheral surface of the bearing rotor member 11, a magnetic flux φ of a magnetic field is concentrated on end portions in the circumferential direction of the magnetic pole surfaces 17d. In contrast to this, when the magnetic pole surfaces 17d are formed as the planar surface, concentration of the magnetic flux φ as described above can be prevented.

Second Embodiment

[Another Configuration of Drive Device]

Figure 5:
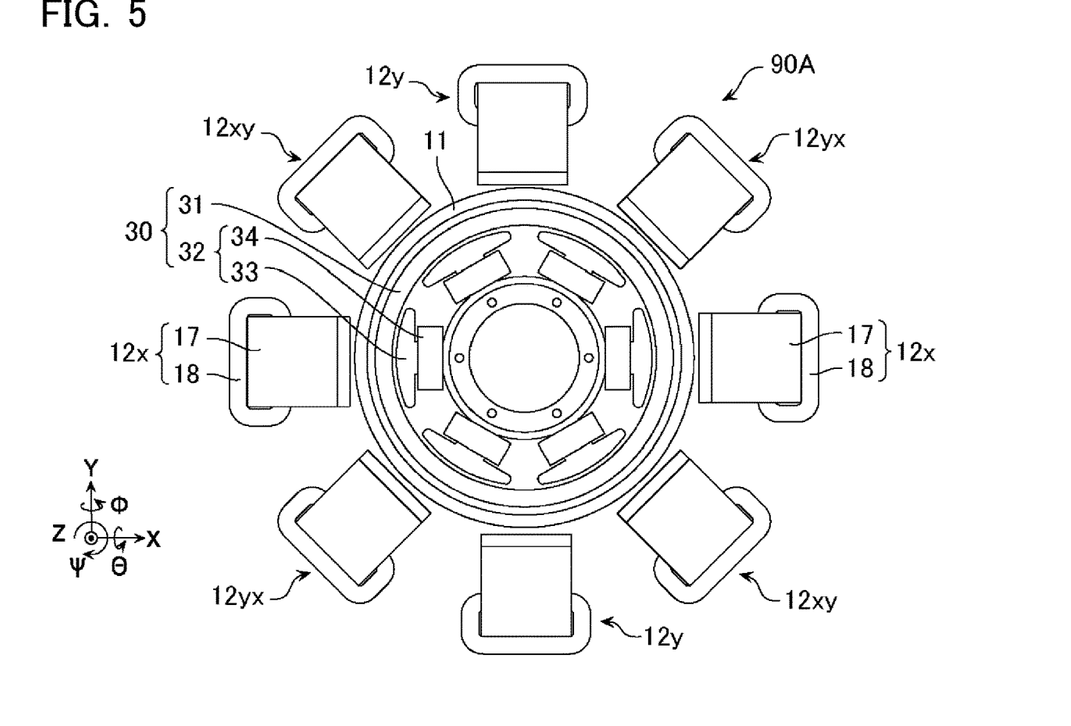
FIG. 5 is a top view schematically illustrating an overall configuration of a drive device according to a second embodiment of the present invention.

FIG. 5 is a top view schematically illustrating an overall configuration of a drive device 90A according to a second embodiment. Here, in the following descriptions including FIG. 5, since the components same as those in the first embodiment are denoted by the same reference numerals, an overlapped description thereof will be omitted below.

That is, as illustrated in FIG. 5, the drive device 90A according to the second embodiment differs from the drive device 90 of the first embodiment in the point that the magnetic bearing 10 includes 8 bearing stator members 12x, 12y, 12xy, and 12yx opposed to the respective directions of the X-axis direction, the Y-axis direction, and oblique 45° directions with respect to the bearing rotor member 11.

With the second embodiment, control in the radial direction can be performed with higher accuracy.

Note that the number of the bearing stator members 12 is not limited to these, and various kinds of forms, such as 6 pieces, 10 pieces, 12 pieces, and 16 pieces, can be employed.

Third Embodiment

[Another Configuration of Magnetic Bearing]

Figure 6:
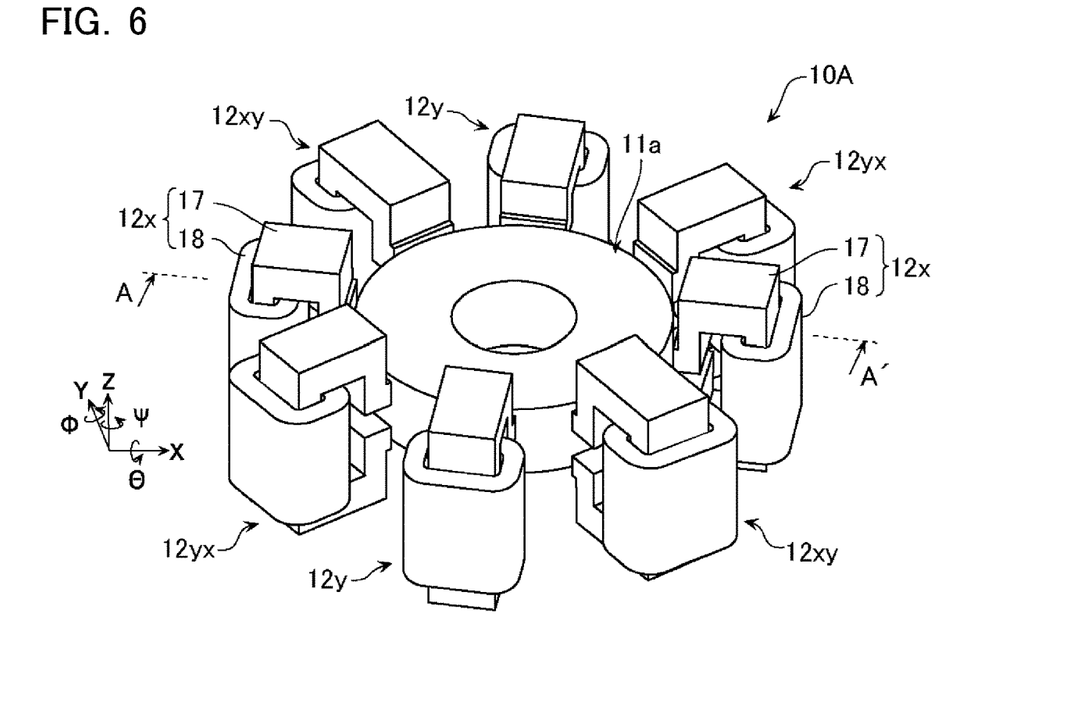
FIG. 6 is a perspective view schematically illustrating a magnetic bearing according to a third embodiment of the present invention.
Figure 7:
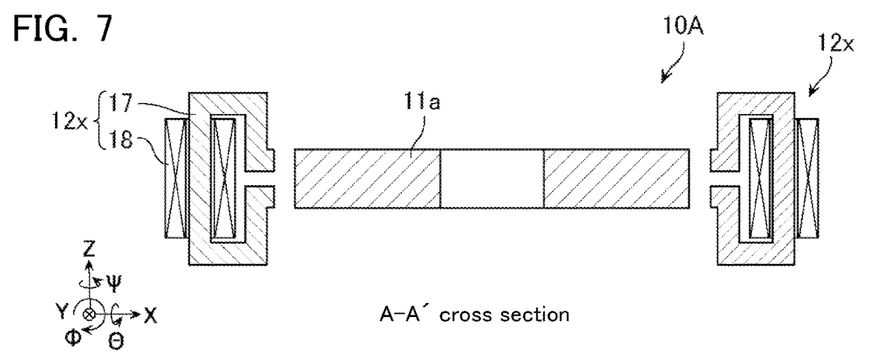
FIG. 7 is a cross-sectional view taken along the line A-A" of FIG. 6.

FIG. 6 is a perspective view schematically illustrating a magnetic bearing 10A according to a third embodiment, and FIG. 7 is a cross-sectional view taken along the line A-A" of FIG. 6.

As illustrated in FIG. 6 and FIG. 7, the magnetic bearing 10A according to the third embodiment differs from the magnetic bearing 10 having the bearing rotor member 11 constituted of the permanent magnet 13 and the yokes 14 and 15 made of electromagnetic soft iron in the point that a bearing rotor member 11a of the rotor 20 is constituted only of, for example, electromagnetic soft iron in a circular shape.

Fourth Embodiment

[Yet Another Configuration of Magnetic Bearing]

Figure 8:
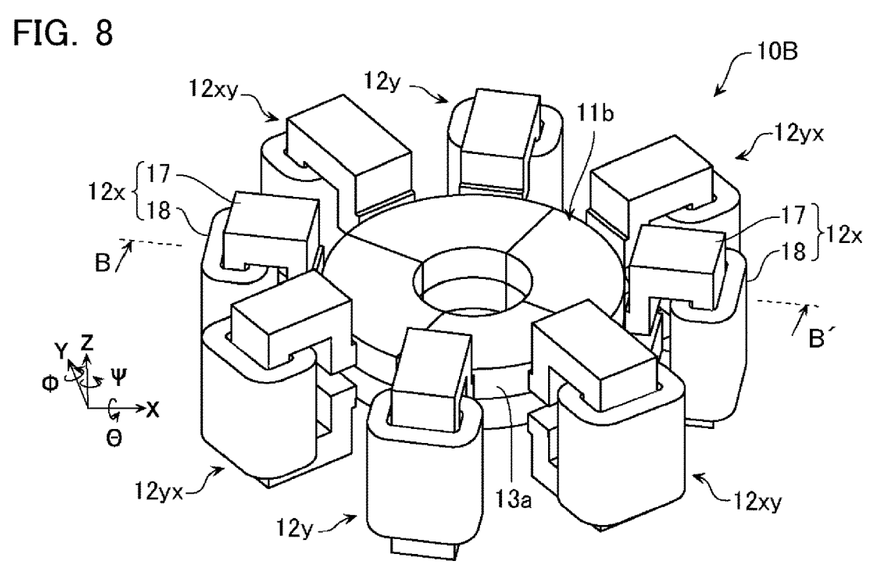
FIG. 8 is a perspective view schematically illustrating a magnetic bearing according to a fourth embodiment of the present invention.
Figure 9:
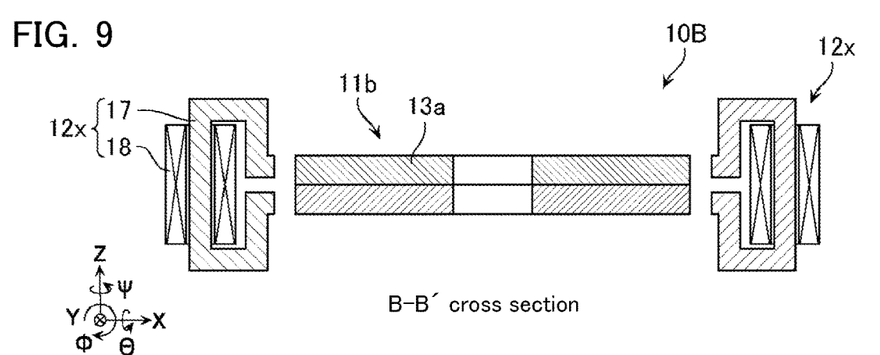
FIG. 9 is a cross-sectional view taken along the line B-B' of FIG. 8.
Figure 10:
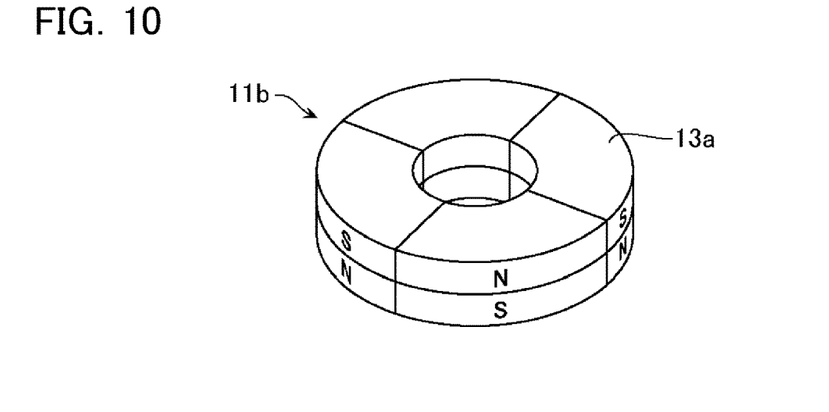
FIG. 10 is a perspective view schematically illustrating a bearing rotor member of the magnetic bearing.

FIG. 8 is a perspective view schematically illustrating a magnetic bearing 10B according to a fourth embodiment of the present invention, FIG. 9 is a cross-sectional view taken along the line B-B' of FIG. 8, and FIG. 10 is a perspective view schematically illustrating a bearing rotor member 11b of the magnetic bearing 10B.

As illustrated in FIG. 8 and FIG. 9, the magnetic bearing 10B according to the fourth embodiment differs from the magnetic bearing 10A having the bearing rotor member 11a constituted only of the electromagnetic soft iron in the point that the bearing rotor member 11b is constituted of, for example, a circular permanent magnet 13a only.

Note that, as illustrated in FIG. 10, the permanent magnet 13a is magnetized in the radial direction such that N-poles and S-poles are alternately arranged in the circumferential direction and an axial direction and is configured to be what is called a quadrupole magnet. With this configuration, since the coil 18 of the bearing stator member 12 of the magnetic bearing 10 can be configured to double as the motor coil 34 of the motor stator 32 of the drive mechanism 30, the drive mechanism 30 can be omitted.

Fifth Embodiment

[Another Configuration of Bearing Rotor Member]

Figure 11:
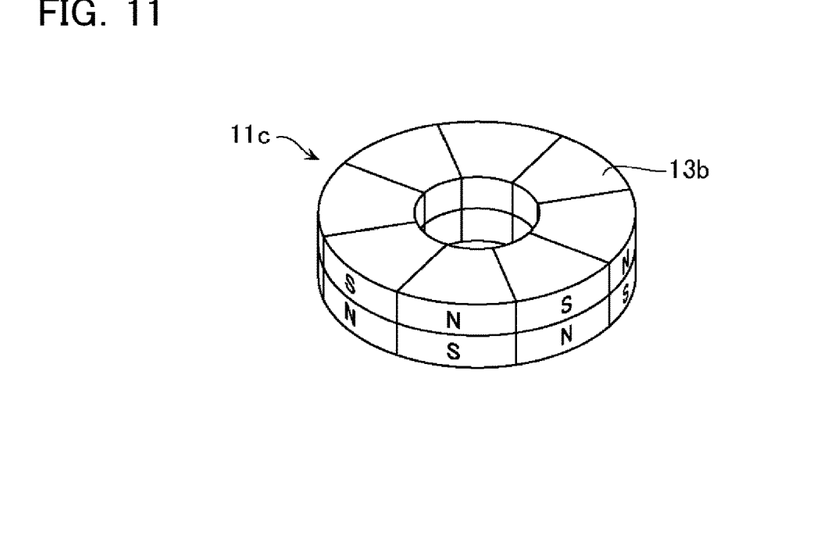
FIG. 11 is a perspective view schematically illustrating a bearing rotor member according to a fifth embodiment of the present invention.

FIG. 11 is a perspective view schematically illustrating a bearing rotor member 11c according to a fifth embodiment of the present invention.

As illustrated in FIG. 11, the bearing rotor member 11c according to the fifth embodiment, which is constituted only of a permanent magnet 13b similarly to the above-described bearing rotor member lib, differs from the fourth embodiment configured to be what is called the quadrupole magnet in the point that the permanent magnet 13b is configured to be what is called an octupole magnet in which magnetic poles of N-poles and S-poles switch around in the axial direction in every 45° along the circumferential direction. With this, an operational advantage similar to the above-described fourth embodiment can be provided.

Sixth Embodiment

[Yet Another Configuration of Bearing Rotor Member]

Figure 12:
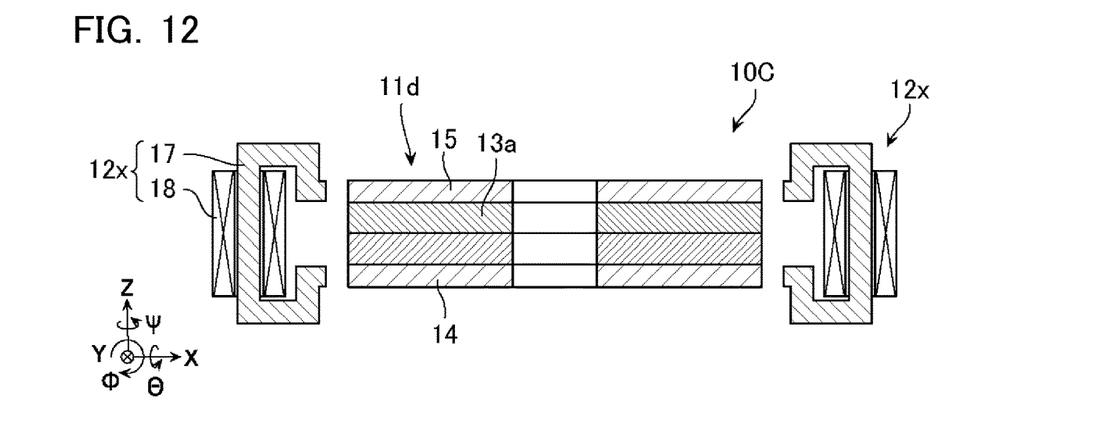
FIG. 12 is a longitudinal cross-sectional view schematically illustrating a bearing rotor member according to a sixth embodiment of the present invention.
Figure 13:
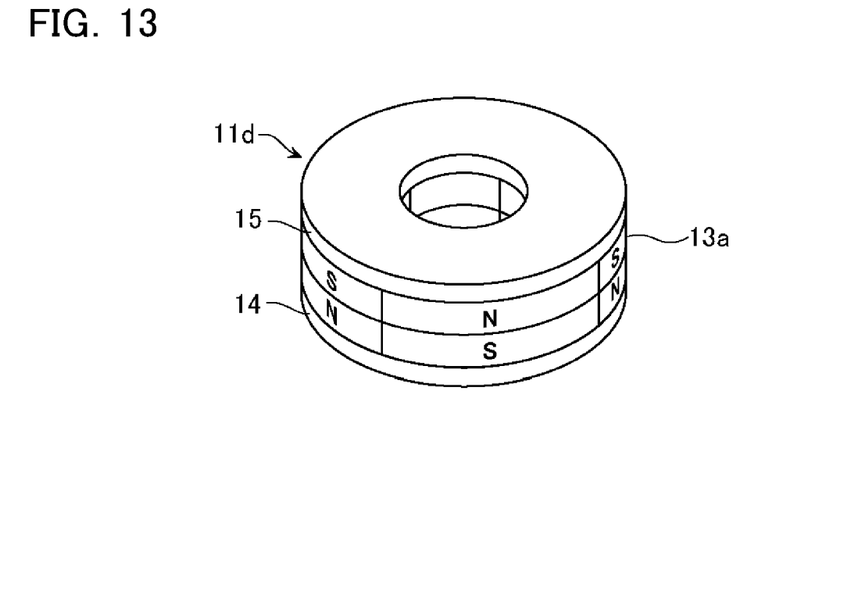
FIG. 13 is a perspective view schematically illustrating a magnetic material portion of FIG. 12.

FIG. 12 is a longitudinal cross-sectional view schematically illustrating a magnetic bearing 10C including a bearing rotor member 11d according to a sixth embodiment of the present invention, and FIG. 13 is a perspective view schematically illustrating the bearing rotor member 11d of FIG. 12.

As illustrated in FIG. 12, the magnetic bearing 10C according to the sixth embodiment has the bearing rotor member 11d having the yokes 14 and 15 made of the electromagnetic soft iron arranged on both sides in the axial direction of the quadrupolar permanent magnet 13a of the fourth embodiment. With this, since the magnetic flux φ of the permanent magnet 13a can be concentrated on the yokes 14 and 15, magnetic holding force of the magnetic bearing 10C itself can be enhanced as compared with a case without the yokes 14 and 15, and the configuration can be made to omit the drive mechanism 30 similarly to the above-described fourth and fifth embodiments.

Note that, although the quadrupole magnet is used in the above-described embodiment, the number of the magnetic poles is not limited to the example.

Seventh Embodiment

[Yet Another Configuration of Magnetic Bearing]

Figure 14:
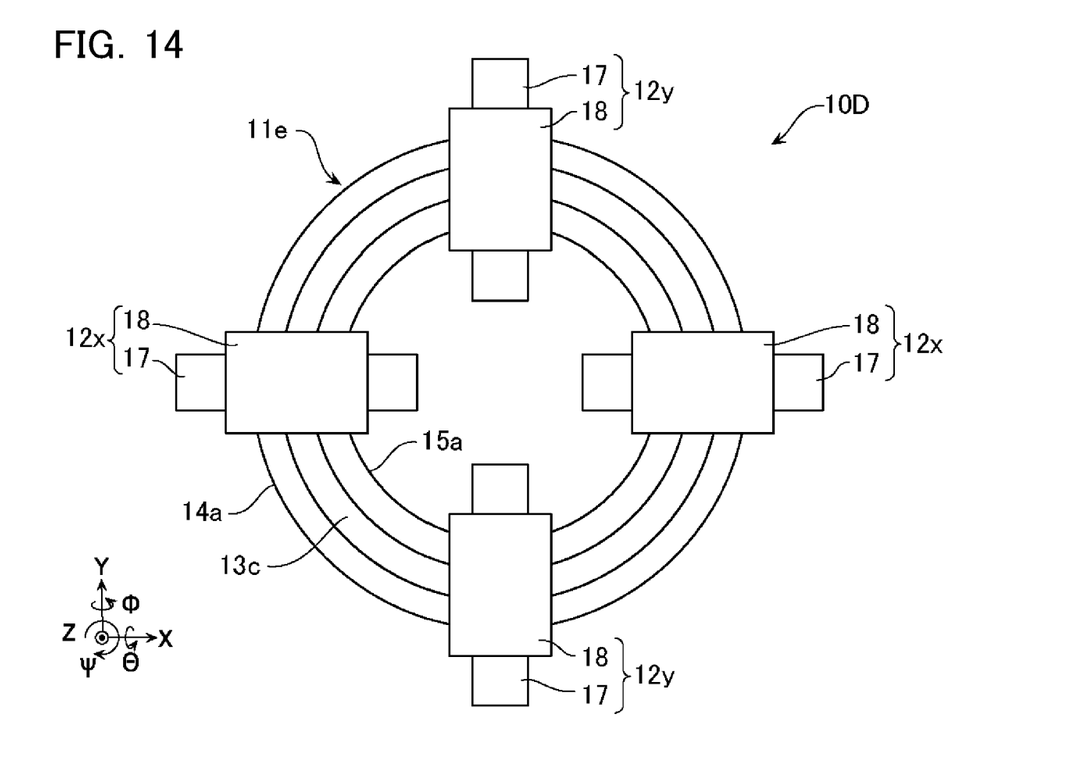
FIG. 14 is a top view schematically illustrating a magnetic bearing according to a seventh embodiment of the present invention.

FIG. 14 is a top view schematically illustrating a magnetic bearing 10D according to a seventh embodiment of the present invention.

Although the magnetic bearings 10 and 10A to 10C of the above-described first to sixth embodiments have the bearing stator member 12 arranged on the outside in the radial direction of the bearing rotor members 11 and 11a to 11d, the seventh embodiment is an example in which the bearing stator member 12 is arranged on one side in the thrust direction of a bearing rotor member 11e.

As illustrated in FIG. 14, in the magnetic bearing 10D according to the seventh embodiment, the bearing rotor member 11e is constituted of an annular permanent magnet 13c, and yokes 14a and 15a formed of electromagnetic soft iron that are respectively arranged on an outer peripheral side and an inner peripheral side of the permanent magnet 13c and sandwich the permanent magnet 13c in the radial direction. The permanent magnet 13c is magnetized in the radial direction. A bias magnetic flux by the permanent magnet 13c causes magnetic poles to appear each on an axial end surface of the yoke 14a on the outside and on an axial end surface of the yoke 15a on the inside. The bearing stator member 12 is arranged on one side in the thrust direction of the bearing rotor member 11e such that the magnetic pole surfaces of the yokes 14a and 15a are opposed to the magnetic pole surfaces 17d positioned at the open end of the core 17 of the bearing stator member 12. In this example, the 4 bearing stator members 12x and 12y are arranged at 4 portions in the circumferential direction at intervals of 90° along one end surface in the axial direction of the bearing rotor member 11e. In this embodiment, a first direction orthogonal to a direction opposed to the bearing rotor member 11e becomes the X-axis direction for the bearing stator member 12x that controls displacement in the X-axis direction and becomes the Y-axis direction for the bearing stator member 12y that controls displacement in the Y-axis direction. Then, the first part 17a around which the coil 18 is wound extends along the X-axis direction or the Y-axis direction.

With the magnetic bearing 10D having such a configuration, the bearing rotor member 11e and the bearing stator member 12 are magnetically coupled in the thrust direction by a loop of the magnetic flux φ from the permanent magnet 13c. Since the bearing stator member 12 employs a configuration in which the core 17 can make the cross-sectional area S of the coil 18 smaller while making the length l of the coil 18 longer as described above under a condition with the same number of turns as the C-shaped core, the restoring force of the rotor 20 can be strengthened and the responsiveness can be improved.

Eighth Embodiment

[Yet Another Configuration of Magnetic Bearing]

Figure 15:
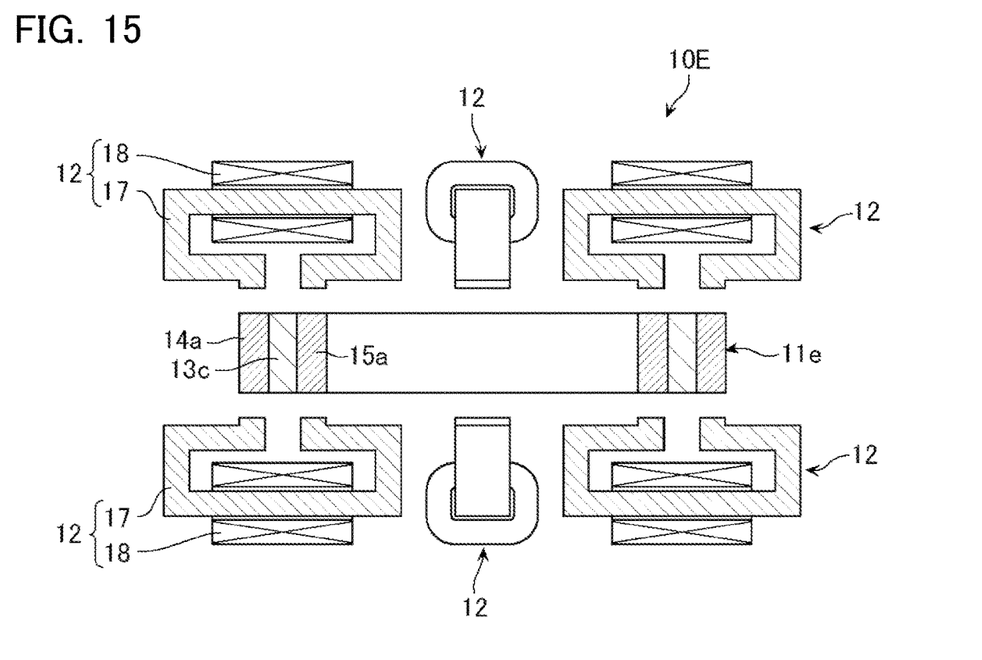
FIG. 15 is a longitudinal cross-sectional view schematically illustrating a magnetic bearing according to an eighth embodiment of the present invention.

FIG. 15 is a longitudinal cross-sectional view schematically illustrating a magnetic bearing 10E according to an eighth embodiment of the present invention.

As illustrated in FIG. 15, the magnetic bearing 10E according to the eighth embodiment indicates an example in which the bearing stator member 12 is arranged on both sides in the thrust direction of the bearing rotor member 11e.

With the magnetic bearing 10E having such a configuration, the bearing rotor member 11e and the bearing stator member 12 are magnetically coupled from both sides in the thrust direction by the loop of the magnetic flux φ from the permanent magnet 13c. Therefore, compared with the magnetic bearing 10D, the restoring force of the rotor 20 can be further strengthened and the magnetic holding force can be further enhanced.

Ninth Embodiment

[Yet Another Configuration of Magnetic Bearing]

Figure 16:
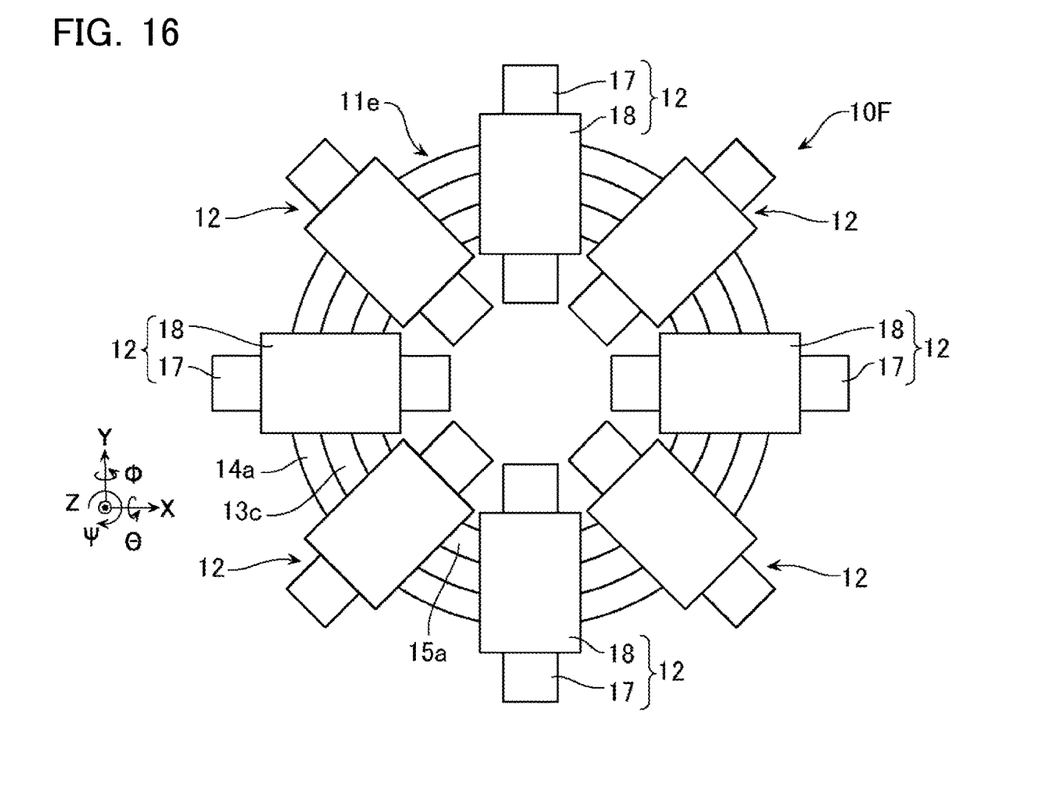
FIG. 16 is a top view schematically illustrating a magnetic bearing according to a ninth embodiment of the present invention.

FIG. 16 is a top view schematically illustrating a magnetic bearing 10F according to a ninth embodiment of the present invention.

In the magnetic bearing 10D of the above-described seventh embodiment, there are a total of 4 bearing stator members 12 which are 2 in the X-axis direction and 2 in the Y-axis direction. In contrast to this, as illustrated in FIG. 16, the magnetic bearing 10F of this embodiment has 8 bearing stator members 12 arranged in the circumferential direction along an end surface in the Z-axis direction of the bearing rotor member 11e. With the magnetic bearing 10F configured as such, support by the magnetic force of the rotor 20 can be conducted more strongly and with higher accuracy compared with the magnetic bearing 10D.

Note that the number of the bearing stator members 12 is not limited to these, and various kinds of forms, such as 6 pieces, 10 pieces, 12 pieces, and 16 pieces, can be employed.

Tenth Embodiment

[Another Configuration of Magnetic Bearing and Drive Device]

Figure 17:
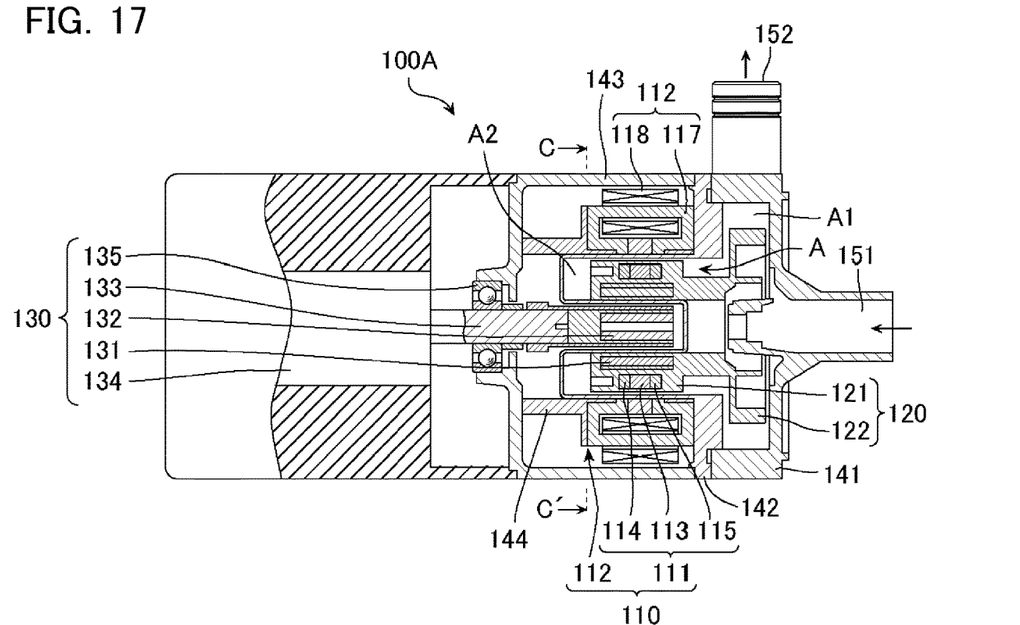
FIG. 17 is a longitudinal cross-sectional view schematically illustrating an overall configuration of a magnetic bearing and a pump equipped with the magnetic bearing according to a tenth embodiment of the present invention with some parts omitted.
Figure 18:
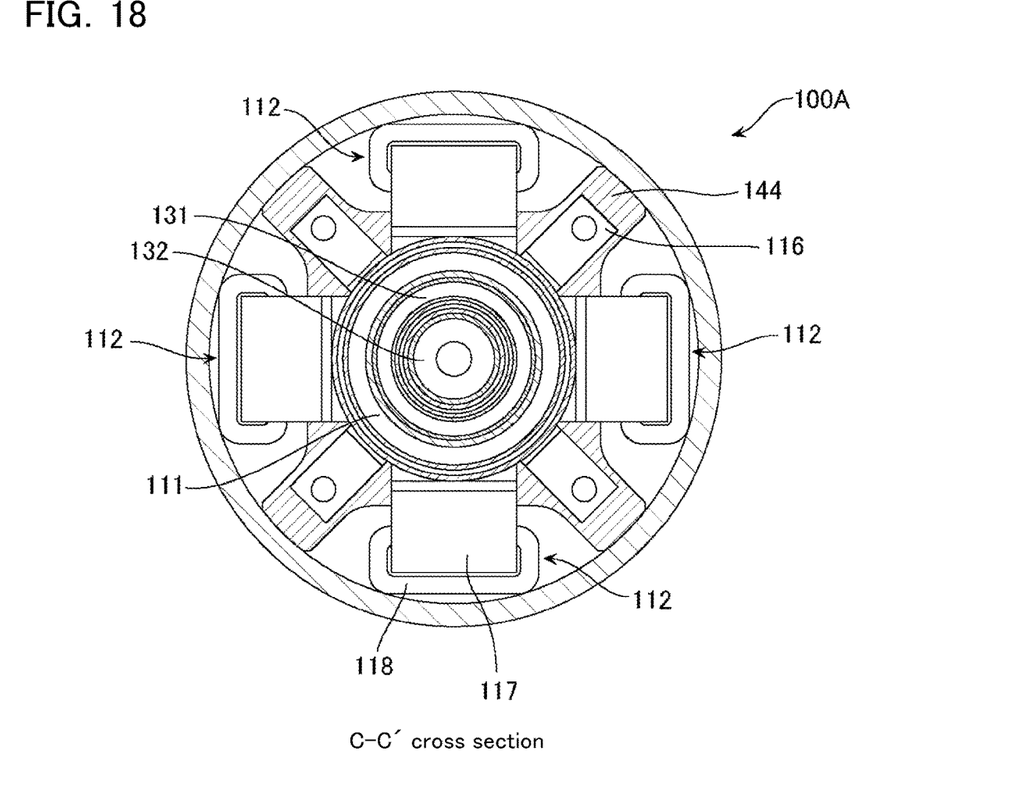
FIG. 18 is a cross-sectional view taken along the line C-C' of FIG. 17.

FIG. 17 is a longitudinal cross-sectional view schematically illustrating an overall configuration, with some parts omitted, of a magnetic bearing 110 and a magnet pump 100A equipped with the magnetic bearing 110 according to a tenth embodiment of the present invention. FIG. 18 is a cross-sectional view taken along the line C-C" of FIG. 17.

As illustrated in FIG. 17 and FIG. 18, although the magnet pump 100A according to the tenth embodiment has a configuration similar to the pump 100 of the first embodiment, it is, for example, the magnet pump 100A for fluid transport. The magnet pump 100A includes a magnetic coupling type drive mechanism 130 besides the magnetic bearing 110.

The magnet pump 100A is formed in a cylindrical shape as a whole and has a front casing 141 on one side of the axial direction. The front casing 141 forms the pump chamber A1 inside, has a cylindrically-shaped suction port 151 in a front center, and has a discharge port 152 on a side surface. A rear casing 142 is connected to a rear end of the front casing 141. The rear casing 142 forms the sealed space A including the pump chamber A1 together with the front casing 141. Further, the rear casing 142 forms the annular space A2 projecting rearward. A cylindrically-shaped bracket 143 is disposed so as to cover an outer periphery of the rear casing 142.

In the sealed space A, a rotor 120 is housed. The rotor 120 has an impeller 122 in a front in the axial direction and an annular bearing/drive unit 121 in a rear. The impeller 122 is housed in the pump chamber A1 and constitutes a pump mechanism together with the pump chamber A1. The bearing/drive unit 121 is housed in the annular space A2. The magnetic bearing 110 that supports the rotor 120 by magnetic force is disposed on an outer peripheral side of the bearing/drive unit 121 of the rotor 120. Further, the drive mechanism 130 that drives the rotor 120 is disposed on an inner peripheral side of the bearing/drive unit 121 of the rotor 120.

The magnetic bearing 110 has a bearing rotor member 111 made of an annular magnetic material and a bearing stator member 112. The bearing rotor member 111 is mounted on the outer peripheral side of the bearing/drive unit 121 of the rotor 120. The bearing stator member 112 is arranged on an outside in the radial direction of the bearing rotor member 111 at a predetermined interval from the bearing rotor member 111. The bearing stator member 112 is mounted between the rear casing 142 and a yoke base 144.

The bearing rotor member 111 has a permanent magnet 113 made of a neodymium magnet formed in, for example, a circular shape and circular yokes 114 and 115 made of electromagnetic soft iron that are concentric with the permanent magnet 113 and arranged so as to sandwich the permanent magnet 113 in the thrust direction (Z-axis direction). The permanent magnet 113 is magnetized such that, for example, an N-pole and an S-pole are opposed in the thrust direction and have the same polarity over a whole circumference in the circumferential direction.

In this embodiment, the bearing stator member 112 is arranged at 4 portions in the circumferential direction of the bearing rotor member 111 at intervals of an angle of 90° as illustrated in FIG. 18. On the yoke base 144, a plurality of displacement sensors 116 (4 in here) that detect displacements in the radial direction, the thrust direction, and each rotation direction of the bearing rotor member 111 are arranged so as to each make an angle of 45° with the bearing stator member 112. Although examples of the displacement sensor 116 include an eddy current type sensor, the displacement sensor 116 is not limited to this and various kinds of sensors can be employed.

The bearing stator member 112 has a core 117 made of a magnetic material, such as a stacked electromagnetic steel plate, and a coil 118 wound around the core 117. A longitudinal cross-sectional shape of the core 117 is approximately C-shaped with the bearing rotor member 111 side as an open end, and a distance between distal ends of the open end is smaller than an axial length of a winding portion of the coil 118. Since the details of the longitudinal cross-sectional shape of the core 117 are similar to those of the first embodiment, the description thereof will be omitted.

The drive mechanism 130 has a driven magnet 131 as an annular driven member, a drive magnet 132 as a drive unit, a motor shaft 133, and a motor 134. The driven magnet 131 is mounted on an inner peripheral side of the bearing/drive unit 121 of the rotor 120. The drive magnet 132 is arranged on an inside of the driven magnet 131 at a predetermined interval from the driven magnet 131. The motor shaft 133 has the drive magnet 132 mounted at a distal end portion and is rotatably supported by a bearing 135. The motor 134 rotatably drives the motor shaft 133. In this example, the driven magnet 131 and the drive magnet 132 are constituted of, for example, neodymium magnets magnetized in 2 poles or 4 poles in the radial direction. Although this example illustrates that the drive magnet 132 and the motor shaft 133 have approximately the same diameter, both do not have to have the same diameter.

In the magnet pump 100A configured in this way, the drive magnet 132 rotates by the motor 134 rotating the motor shaft 133, and the driven magnet 131 is driven by magnetic force of the drive magnet 132 to cause the rotor 120, that is, the impeller 122 to rotate contactlessly. Similarly to the magnetic bearing 10 of the first embodiment, the magnetic bearing 110 controls 5 degrees of freedom in the radial direction, the thrust direction, and 2 radial rotation axis directions. Therefore, with this embodiment as well, a restoring force and responsiveness of the rotor 120 can be enhanced.

Eleventh Embodiment

[Another Configuration of Magnetic Bearing]

Figure 19:
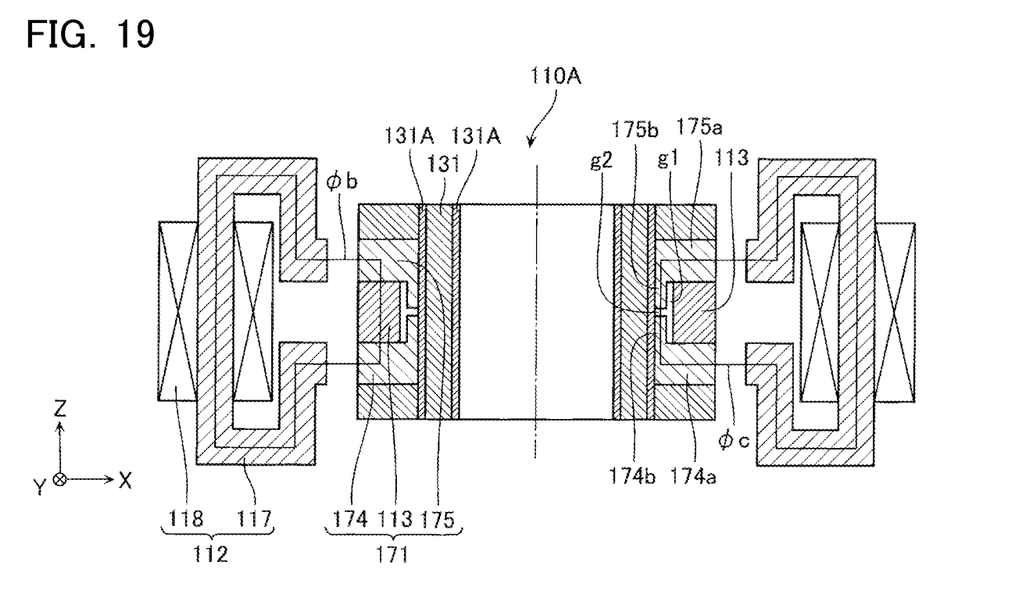
FIG. 19 is a longitudinal cross-sectional view schematically illustrating a magnetic bearing according to an eleventh embodiment of the present invention.

FIG. 19 is a longitudinal cross-sectional view schematically illustrating a magnetic bearing 110A according to an eleventh embodiment. As illustrated in FIG. 19, the magnetic bearing 110A according to the eleventh embodiment has a bearing rotor member 171 having a configuration that is different from the bearing rotor member 111 of the magnetic bearing 110 according to the tenth embodiment.

That is, the bearing rotor member 171 has the permanent magnet 113 in, for example, a circular shape, and a pair of circular yokes 174 and 175 that are concentric with the permanent magnet 113 and arranged so as to sandwich the permanent magnet 113 from both sides in the thrust direction (Z-axis direction). In this embodiment, a longitudinal cross-sectional shape of the pair of yokes 174 and 175 is approximately U-shaped with the bearing stator member 112 side as an open end and a center in the Z-axis direction being cut off.

Specifically, as illustrated in FIG. 19, the longitudinal cross-sectional shape of the pair of yokes 174 and 175 has fourth parts 174a and 175a and a pair of fifth parts 174b and 175b. The fourth parts 174a and 175a extend to a second direction (radial direction (X-axis direction) inhere) orthogonal to the Z-axis direction so as to cover both end surfaces of a first direction (Z-axis direction in here) of the permanent magnet 113. The fifth parts 174b and 175b extend from end portions of the fourth parts 174a and 175a on an opposite side of the bearing stator member 112 in a direction approaching each other in the Z-axis direction. Inner peripheral portions of the fourth parts 174a and 175a project inward with respect to an inner peripheral portion of the permanent magnet 113. A first gap g1 is formed between the fifth parts 174b and 175b and the permanent magnet 113. Further, a second gap g2 is provided between opposed distal end portions of the pair of fifth parts 174b and 175b.

With this shape, since the first gap g1 can prevent both magnetic poles of the permanent magnet 113 from approaching too closely to the fifth parts 174b and 175b, a bias magnetic flux φb by the permanent magnet 113 can be stably supplied to the bearing stator member 112. Further, since a magnetic circuit by the fifth parts 174b and 175b having a small magnetic reluctance is formed in parallel with the permanent magnet 113 having a large magnetic reluctance, a control magnetic flux φc generated by the coil 118 can be passed through to the bearing rotor member 171 with as little loss as possible. However, if there is no second gap g2, both of the magnetic poles of the permanent magnet 113 are short-circuited via the fifth parts 174b and 175b. Therefore, it is preferred to appropriately set a width of the second gap g2 in consideration of a balance between a stable supply of the bias magnetic flux φb to the bearing stator member 112 side and the magnetic reluctance of the magnetic circuit through which the control magnetic flux φc passes.

The magnetic bearing 110A of this embodiment can be applied to the eighth embodiment illustrated in FIG. 15. Further, the magnetic bearing 110A may be combined with a bearing stator member having a general U-shaped core illustrated in FIG. 20. However, for example, when the magnetic bearing 110A is applied to the above-described magnet pump 100A, combining especially with the above-described bearing stator member 112 (bearing stator member 12) having the first part 17a to the third parts 17c allows a rotation control of the rotor 120 to be conducted accurately corresponding to its operation situation. Note that, for example, when the magnetic bearing 110A is applied to the magnet pump 100A, the driven magnet 131 driven with a drive magnet (not illustrated) is arranged on an inner peripheral side of the bearing rotor member 171 in a state of being sandwiched in the radial direction by non-magnetic bodies 131A.

Although several embodiments of the present invention have been described, these embodiments are presented as examples, and are not intended to limit the scope of the invention. These new embodiments can be implemented in other various forms, and various omissions, replacements, and changes can be made in a range that does not depart from the gist of the invention. These embodiments and their modifications are included in the scope and the gist of the invention, and are included in the scope of the invention described in the claims and their equivalents.

DESCRIPTION OF REFERENCE NUMERAL

10 Magnetic bearing
11 Bearing rotor member
12 Bearing stator member
13 Permanent magnet
14, 15 Yoke
16 Displacement sensor
17 Core
17a First part
17b Second part
17c Third part
18 Coil
20 Rotor
30 Drive mechanism
90 Drive device
100 Pump

The invention claimed is:

1. A magnetic bearing contactlessly supporting a rotor by magnetic force, comprising:
a bearing rotor member made of a magnetic material disposed in the rotor; and
a bearing stator member arranged around the bearing rotor member, wherein
the bearing stator member includes a core made of a magnetic material and a coil wound around the core, and
a longitudinal cross-sectional shape of the core has:
a first part extending in a first direction orthogonal to a direction opposed to the bearing rotor member, and wound around with the coil;
a pair of second parts extending from both end portions in the first direction of the first part toward the bearing rotor member side and subsequently extending in a direction approaching each other in the first direction; and
a pair of third parts extending from respective distal end portions of the pair of second parts toward the bearing rotor member side, wherein
the bearing rotor member includes a permanent magnet supplying a bias magnetic flux to a magnetic circuit formed by the bearing rotor member and the core, and
a length in the first direction of the coil wound around the first part is greater than a distance between opposed surfaces in the first direction of the pair of third parts.

2. The magnetic bearing according to claim 1, wherein
a distance between surfaces on opposite sides of opposed surfaces in the first direction of the pair of third parts is smaller than a length in the first direction of the first part.

3. The magnetic bearing according to claim 1, wherein
the distance between surfaces on opposite sides of opposed surfaces in the first direction of the pair of third parts is approximately equal to a length in the first direction of the bearing rotor member opposed to the third parts.

4. The magnetic bearing according to claim 1, wherein the bearing rotor member includes:
the permanent magnet in a circular shape; and
a pair of circular yokes arranged so as to sandwich the permanent magnet in the first direction, wherein
a longitudinal cross-sectional shape of the pair of yokes has:
  a pair of fourth parts covering both end surfaces in the first direction of the permanent magnet and extending toward an opposite side of the bearing stator member; and
  a pair of fifth parts extending from end portions of the pair of fourth parts on an opposite side of the bearing stator member in a direction approaching each other in the first direction, wherein
  a first gap is formed between the fifth parts and the permanent magnet, and
  a second gap is provided between respective distal end portions of the pair of fifth parts opposed to each other.

5. The magnetic bearing according to claim 1, wherein
a plurality of the bearing stator members are arranged on an outside in a radial direction of the bearing rotor member and are each opposed to the bearing rotor member in the radial direction.

6. The magnetic bearing according to claim 1, wherein
a plurality of the bearing stator members are arranged on at least one side in an axial direction of the bearing rotor member and are each opposed to the bearing rotor member in the axial direction.

7. A drive device comprising:
a rotor,
a magnetic bearing supporting the rotor by magnetic force, and
a drive mechanism rotatably driving the rotor, wherein the magnetic bearing includes:
  a bearing rotor member made of a magnetic material disposed in the rotor; and
  a bearing stator member arranged around the bearing rotor member, wherein
  the bearing stator member includes a core made of a magnetic material and a coil wound around the core, and
  a longitudinal cross-sectional shape of the core has:
    a first part extending in a first direction orthogonal to a direction opposed to the bearing rotor member, and wound around with the coil;
    a pair of second parts extending from both end portions in the first direction of the first part toward the bearing rotor member side and subsequently extending in a direction approaching each other in the first direction; and
    a pair of third parts extending from respective distal end portions of the pair of second parts toward the bearing rotor member side, wherein
  the bearing rotor member includes a permanent magnet supplying a bias magnetic flux to a magnetic circuit formed by the bearing rotor member and the core, and
  a length in the first direction of the coil wound around the first part is greater than a distance between opposed surfaces in the first direction of the pair of third parts.

8. The drive device according to claim 7, wherein the bearing rotor member includes:
the permanent magnet in a circular shape; and
a pair of circular yokes arranged so as to sandwich the permanent magnet in the first direction, wherein
a longitudinal cross-sectional shape of the pair of yokes has:
  a pair of fourth parts covering both end surfaces in the first direction of the permanent magnet and extending toward an opposite side of the bearing stator member; and
  a pair of fifth parts extending from end portions of the pair of fourth parts on an opposite side of the bearing stator member in a direction approaching each other in the first direction, wherein
  a first gap is formed between the fifth parts and the permanent magnet, and
  a second gap is provided between respective distal end portions of the pair of fifth parts opposed to each other.

9. The drive device according to claim 7, wherein the drive mechanism includes:
a driven member arranged on an inside in a radial direction of the bearing rotor member in the rotor; and
a drive unit arranged on an inside of the driven member and magnetically coupled with the driven member to drive the rotor.

10. A pump comprising:
a rotor;
a magnetic bearing supporting the rotor by magnetic force;
a drive mechanism rotatably driving the rotor; and
a pump mechanism that includes an impeller attached to the rotor, wherein the magnetic bearing includes:
  a bearing rotor member made of a magnetic material disposed in the rotor; and
  a bearing stator member arranged around the bearing rotor member, wherein
  the bearing stator member includes a core made of a magnetic material and a coil wound around the core,
  a longitudinal cross-sectional shape of the core has:
    a first part extending in a first direction orthogonal to a direction opposed to the bearing rotor member, and wound around with the coil;
    a pair of second parts extending from both end portions in the first direction of the first part toward the bearing rotor member side and subsequently extending in a direction approaching each other in the first direction; and
    a pair of third parts extending from respective distal end portions of the pair of second parts toward the bearing rotor member side, wherein
  the bearing rotor member includes a permanent magnet supplying a bias magnetic flux to a magnetic circuit formed by the bearing rotor member and the core, and
  a length in the first direction of the coil wound around the first part is greater than a distance between opposed surfaces in the first direction of the pair of third parts.

11. The pump according to claim 10, wherein the bearing rotor member includes:
- the permanent magnet in a circular shape; and
- a pair of circular yokes arranged so as to sandwich the permanent magnet in the first direction, wherein
- a longitudinal cross-sectional shape of the pair of yokes has:
  - a pair of fourth parts covering both end surfaces in the first direction of the permanent magnet and extending toward an opposite side of the bearing stator member; and
  - a pair of fifth parts extending from end portions of the pair of fourth parts on an opposite side of the bearing stator member in a direction approaching each other in the first direction, wherein
  - a first gap is formed between the fifth parts and the permanent magnet, and
  - a second gap is provided between respective distal end portions of the pair of fifth parts opposed to each other.

* * * * *